United States Patent [19]

Madison et al.

[11] Patent Number: 5,078,907

[45] Date of Patent: Jan. 7, 1992

[54] UNSYMMETRICAL DICARBOXYLIC ESTERS AS BLEACH PRECURSORS

[75] Inventors: Stephen A. Madison, Valley Cottage; Pamela C. Lam, Congers, both of N.Y.

[73] Assignee: Lever Brothers Company, Division of Conopco, Inc., New York, N.Y.

[21] Appl. No.: 430,531

[22] Filed: Nov. 1, 1989

[51] Int. Cl.$^5$ .................. C09K 3/00; C07C 69/76; C07C 69/34

[52] U.S. Cl. .................. 252/186.39; 252/186.38; 560/86; 560/146

[58] Field of Search .................. 560/86, 146; 252/186.38, 186.39

[56] References Cited

U.S. PATENT DOCUMENTS

| | | | |
|---|---|---|---|
| 2,955,905 | 10/1960 | Davies et al. | 252/99 |
| 3,076,837 | 2/1963 | Mills | 560/86 |
| 4,283,301 | 8/1981 | Diehl | 252/102 |
| 4,397,757 | 8/1983 | Bright et al. | 252/186.41 |
| 4,412,934 | 11/1983 | Chung et al. | 252/186.38 |
| 4,451,664 | 5/1984 | Ranade | 560/142 |
| 4,486,327 | 12/1984 | Murphy et al. | 252/94 |
| 4,751,015 | 6/1988 | Humphreys et al. | 252/99 |
| 4,904,406 | 2/1990 | Darwent et al. | 252/186.39 |
| 4,933,103 | 6/1990 | Aoyagi et al. | 252/186.38 |

FOREIGN PATENT DOCUMENTS

| | | | |
|---|---|---|---|
| 0049686 | 4/1982 | European Pat. Off. | 560/86 |
| 0098129 | 1/1984 | European Pat. Off. | |
| 0106584 | 4/1984 | European Pat. Off. | |
| 0106634 | 4/1984 | European Pat. Off. | |
| 0120591 | 10/1984 | European Pat. Off. | |
| 0153222 | 8/1985 | European Pat. Off. | |
| 0153223 | 8/1985 | European Pat. Off. | |
| 0163331 | 12/1985 | European Pat. Off. | |
| 0166571 | 1/1986 | European Pat. Off. | |
| 0170386 | 2/1986 | European Pat. Off. | |
| 0185522 | 6/1986 | European Pat. Off. | |
| 0202698 | 11/1986 | European Pat. Off. | |
| 1001895 | 8/1965 | United Kingdom | 560/86 |

*Primary Examiner*—Robert L. Stoll
*Assistant Examiner*—Joseph D. Anthony
*Attorney, Agent, or Firm*—Milton L. Honig

[57] ABSTRACT

A bleach precursor compound, its peroxygen derivative, and detergent compositions containing these materials are disclosed herein. The bleach precursors structurally comprise a pair of different diesters, one ester containing an electrically-charged functional group. Perhydrolysis of the precursor in the presence of hydrogen peroxide and a basic aqueous media generates a peroxycarboxylic acid.

29 Claims, No Drawings

UNSYMMETRICAL DICARBOXYLIC ESTERS AS BLEACH PRECURSORS

BACKGROUND OF THE INVENTION

1. Field of the Invention

The invention relates to novel bleach precursors, peracids generated therefrom and use of these materials in detergent compositions.

2. The Related Art t active oxygen-releasing compounds

It is well known that active oxygen-releasing compounds are effective bleaching agents. These compounds are frequently incorporated into detergent compositions for stain and soil removal. Unlike the traditional sodium hypochlorite bleaches, oxygen-releasing compounds are less aggressive and thus more compatible with detergent compositions. They have, however, an important limitation; the activity of these compounds is extremely temperature dependent. Thus, oxygen-releasing bleaches are essentially only practical when the bleaching solution is heated above 60° C. Extremely high amounts of the active oxygen-releasing compounds must therefore be added to the system to achieve any bleach effect. Although this would indicate the desirability of high temperature operation, high temperatures are both economically and practically disadvantageous.

Automatic household washing machines for cleaning laundry are normally operated at wash-water temperatures below 60° C. Consequently, there has developed a need for substances which promote release of active oxygen at temperatures below 60° C. These substances are generally referred to in the art as bleach precursors, although they have also been called promoters and activators. Normally, bleach precursors are used in conjunction with persalts capable of releasing hydrogen peroxide in aqueous solution, perborate being the most widely used persalt.

Typically, the precursor is a reactive compound such as a carboxylic acid ester that in alkaline detergent solution containing a source of hydrogen peroxide, e.g. a persalt, will generate the corresponding peroxy acid. The reaction involves nucleophilic substitution onto the precursor by hydroperoxy anions (HOO—) and is facilitated by precursors having good leaving groups. Often the reaction is referred to as a perhydrolysis.

One of the earliest patents in the area of precursor chemistry was U.S. Pat. No. 2,955,905 (Davies et al) which discloses esters as precursors such as phenyl acetate, phenyl benzoate, p-nitrobenzaldehyde diacetate and glycollic aldehyde triacetate among a wide variety of compounds.

Other patents of note are U.S. Pat. No. 4,283,301 (Diehl) which discloses a peroxygen bleach and a precursor of the general formula:

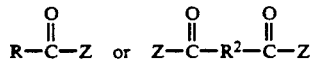

wherein R is an alkyl chain containing from 5 to 13 carbon atoms, R² is an alkyl chain containing from 4 to 24 carbon atoms and each Z is a leaving group as defined therein.

U.S. Pat. No. 4,751,015 (Humphreys et al) reports a series of quaternary ammonium substituted carbonate salts, one example of which has a choline moiety and a phenol sulphonate group at opposite ends of the carbonate function. Bis type compounds are also generically suggested at column 3, line 50.

U.S. Pat. No. 4,412,934 (Chung et al) reports compositions incorporating bleach precursors of the general formula:

wherein R is an alkyl group containing from 5 to 18 carbon atoms and L is a leaving group.

Similar disclosures are found in U.S. Pat. No. 4,486,327 (Murphy et al), EP No. 0 098 129 (Hardy et al), EP No. 0 106 584 (Hartman), EP No. 0 106 634 (Chung et al), EP No. 0 120 591 (Hardy et al), EP No. 0 163 331 (Burns et al), EP No. 0 166 571 (Hardy et al), Ep No. 0 185 522 (Fong et al), EP No. 0 170 386 (Burns et al) EP No. 0 153 222 (Moyne et al), EP No. 0 153 223 (Moyne et al) and EP No. 0 202 698 (Nollet et al).

While the aforementioned precursors have all been reported effective at stain removal, there is still a need for more efficient systems. Stain removal efficiency may be improved either by a precursor that generates equivalent bleach at a lower precursor molar level or operates at lower levels of peroxide source. Not only do lower levels of peroxide source or precursor provide better economics, they also permit increased flexibility in detergent formulation.

Consequently, it is an object of the present invention to provide a detergent-bleach composition with a precursor that permits bleaching over a wide temperature range including that of under 60° C.

It is another object of the present invention to provide certain novel bleach precursors which have hitherto not been described in the art.

Another object of the present invention is to provide a precursor that can be economically synthesized from readily available starting materials and in a minimum number of synthetic steps.

A still further object of the present invention is to provide novel peroxy acids generated from the bleach precursors by perhydrolysis with hydrogen peroxide or persalts.

SUMMARY OF THE INVENTION

A bleach precursor compound is provided having the formula

wherein:

A is a C₁-C₁₂ radical which is selected from the group consisting of alkylene, alkenylene, alkynylene, cycloalkylene, cycloalkenylene, alkarylene, arylene and mixtures thereof;

X is a C₁-C₂₀ radical the hydrocarbyl portion of which is different from that of Z and selected from the group consisting of alkyl, alkenyl, alkynyl, cycloalkyl, cycloalkenyl, alkaryl, aryl, quaternized heterocyclic ring system and quaternary ammonium substituted derivatives thereof;

Z is a leaving group whose conjugate acid has a pKa from about 6 to 13.

A peroxygen acid is also provided having the formula:

 (II)

wherein:

X and A are as defined above with the proviso that A has at least two carbon atoms.

Furthermore, a detergent-bleaching composition is provided comprising:
(i) from 1 to 60% of a peroxygen compound capable of yielding hydrogen peroxide in an aqueous solution;
(ii) from 0.1 to to 40% of the bleach precursor of formula I described hereinabove;
(iii) from 0 to 50% of a surfactant; and
(iv) from 0 to 70% of a detergent builder.

DETAILED DESCRIPTION OF THE INVENTION

There have now been discovered a novel group of compounds having the formula:

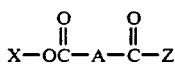 (I)

which meet many of the objectives outlined. A key aspect of the precursors as seen from structure I is that they are functionalized with two different ester groups. One of the esters carries a readily separable leaving group, the conjugate acid of which has a $pK_a$ in the range of from about 6 to 13, preferably from about 7 to 11, optimally between about 8 to 11. The other ester is a group readily attractive toward stains.

There are certain advantages to the compounds of this invention. Hydrophobic-hydrophilic properties can easily be manipulated by selecting appropriate alcohols to form the esters. Furthermore, the presence of ester linkages renders these materials more susceptible to downstream biodegradation.

Leaving group Z must be of a structure appropriate to facilitate reaction of the bleach precursor with hydrogen peroxide in basic aqueous solution to generate the peroxycarboxylic acid of formula II.

Effective leaving groups will be those that induce rapid formation of the peroxycarboxylic acid in the presence of a peroxygen source under practical conditions, e.g. in detergent solution during laundering of clothes. Generally, Z must be an electron attracting structure which promotes successful nucleophilic attack by the perhydroxide anion.

Many and diverse leaving group structures have been described in the patent literature and are useful for this invention. For example, U.S. Pat. No. 4,412,934, U.S. 4,483,778, EP 170,386 and EP 166,571 provide examples of desirable leaving groups, and are herein incorporated by reference.

Illustrative of the leaving structures Z are those selected from the group consisting of:

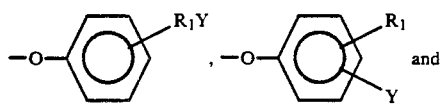

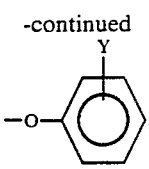

wherein $R_1$ is a $C_1$-$C_{12}$ alkyl or alkylene group or hydrogen; Y is a water solubilizing group. Preferred solubilizing groups are $-SO_3^- M^+$, $-COO^{-M}+$, $-N^+(R)_3B^-$, and mixtures thereof; wherein $M^+$ is an alkali metal, ammonium or alkyl or hydroxyalkyl substituted ammonium cation; and $B^-$ is a halide, hydroxide, phosphate, sulfate, methyl sulfate or acetate anion.

Most preferred of the leaving groups is the phenol sulfonate group. Sodium, potassium and ammonium cations are the preferred counterions to phenol sulfonate.

With respect to X, this structure should be a leaving group whose conjugate acid has a pKa that is greater than 14, preferably ranging from about 15 to about 30.

In particular it is desirable X be a $C_2$-$C_{12}$ alkyl radical, preferably higher than $C_3$. Advantageously, X may include a quaternary ammonium group substituent such as trialkylammonium cation, especially in the form of a choline ester. X may also be a quaternized form of a heterocyclic ring system such as a substituted or unsubstituted pyridine, morpholine, pyrrolidine, piperidine and piperazine radical. Likewise, Z may comprise a heterocyclic ring system similar to the aforementioned nitrogen-containing heterocycles.

With regard to the bridging radical A, this is preferably a substituted or unsubstituted phenylene or a $C_2$-$C_{10}$ alkylene unit, with the former being much preferred.

Preferred structures of precursor I are best expressed in terms of the diacids and alcohols forming the diester. Diacids such as phthalic, terephthalic, succinic and glutaric acids are highly preferred because of their ready commercial availability. Of course, acids such as azelaic, isophthalic, dodecanedioic and similar materials could also function as appropriate substrates. Alcohols that may be used with particular advantage are methanol, ethanol, n-propanol, n-butanol, n-hexanol and choline. Other alcohols may also be used including branched $C_4$-$C_{10}$ and linear $C_8$-$C_{12}$ alcohols to increase hydrophobicity.

The following compounds are illustrative of precursors within the present invention. It is also to be understood that upon perhydrolysis elimination of the leaving group, as defined above, there will remain an organic peroxygen acid derivative of the structures outlined below.

Sodium 4-(4-methoxycarbonyl)benzoyloxybenzenesulfonate

Sodium 4-(4-ethoxycarbonyl)benzoyloxybenzenesulfonate

Sodium 4-(4-propoxycarbonyl)benzoyloxybenzenesulfonate

Sodium 4-(4-butoxycarbonyl)benzoyloxybenzenesulfonate

Sodium 4-(4-hexyloxycarbonyl)benzoyloxybenzenesulfonate

Phenyl 4-cholyloxycarbonylbenzoate, chloride salt
4-(2-Cholyloxycarbonyl)benzoyloxybenzenesulfonate Monocholyl mono-4-sulfophenyl succinate Monocholyl mono-4-sulfophenyl glutarate Excellent yields of peracid were achieved with the above compounds. Almost all of these materials provided outstanding bleaching.

The foregoing precursors may be incorporated into detergent bleach compositions which require as an essential component a peroxygen bleaching compound capable of yielding hydrogen peroxide in an aqueous solution.

Typically, the ratio of hydrogen peroxide (or a peroxygen compound generating the equivalent amount of $H_2O_2$) to precursor will range from about 0 5:1 to 10:1, preferably 1:1 to 4:1, most preferably 1:1 to less than 1.5:1.

Hydrogen peroxide sources are well known in the art. They include the alkali metal peroxides, organic peroxides such as urea peroxide, and inorganic persalts, such as the alkali metal perborates, percarbonates, perphosphates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions. Rapid dissolution is believed to permit formation of higher levels of percarboxylic acid which would enhance surface bleaching performance.

A detergent formulation containing a bleach system consisting of an active oxygen releasing material and a novel compound of the invention will usually also contain surface-active materials, detergency builders and other known ingredients of such formulations.

The surface-active material may be naturally derived, such as soap, or a synthetic material selected from anionic, nonionic, amphoteric, zwitterionic, cationic actives and mixtures thereof Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 1% to 40% by weight of the composition, most preferably 4% to 25%.

Synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_9$–$C_{20}$) benzene sulphonates, benzene sulphonates; sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6C_{22}$) phenols, generally 5–25 EO, i.e. 5–25 units of ethylene oxides per molecule; the condensation products of aliphatic ($C_8$–$C_{18}$) primary or secondary linear or branched alcohols with ethylene oxide, generally 6–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which re used are preferably the sodium, or less desirably potassium, salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 15%, are used to give a beneficial effect on detergency This is particularly valuable in compositions used in hard water when the soap acts as a supplementary builder The detergent compositions of the invention will normally also contain a detergency builder. Builder materials may be selected from (1) calcium sequestrant materials, (2) precipitating materials, (3) calcium ion-exchange materials and (4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetalcarboxylates as disclosed in U.S. Pat. No. 4,144,225 and U.S. Pat. No. 4,146,495.

Examples of precipitating builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, oxydisuccinates or mixtures thereof.

These builder materials may be present at a level of, for example, from 5 to 80% by weight, preferably from 10 to 60% by weight.

When the peroxygen compound and bleach precursor are dispersed in water, a peroxy acid (II) is generated which should deliver from about 0.1 to about 50 ppm active oxygen per liter of water; preferably oxygen delivery should range from 2 to 15 ppm. Surfactant should be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in fabric washing detergent compositions. Examples of these additives include lather boosters such as alkanolamides, particularly the monoethanolamides derived from palm kernel fatty acids and coconut fatty acids, lather depressants such as alkyl phosphates and silicones, anti-redeposition agents such as sodium carboxymethylcellulose and alkyl or substituted alkylcellulose ethers, other stabilizers such as ethylene diamine tetraacetic acid, fabric softening agents, inorganic salts such as sodium sulphate, and, usually present in very small amounts, fluorescent agents, perfumes, enzymes such as proteases, cellulases, lipases and amylases, germicides and colorants.

The bleach precursors and their peroxycarboxylic acid derivatives described herein are useful in a variety of cleaning products. These include laundry detergents, laundry bleaches, hard surface cleaners, toilet bowl cleaners, automatic dishwashing compositions and even denture cleaners. Precursors of the present invention can be introduced in a variety of product forms including powders, on sheets or other substrates, in pouches, in tablets or in non-aqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Preparation of Monopotassium Methyl Terephthalate

This procedure is a modification of the one described by B. W. Hotten (Ind. Eng. Chem. 1957, 49, 1691-4).

To a three-necked 50 ml round bottom flask equipped with a mechanical stirrer, reflux condenser and an addition funnel topped with a drying tube containing indicating Drierite ® were added 2.70 gm (0.0139 mole) of dimethyl terephthalate (ex Aldrich Chemical Co.) and 15 ml of toluene. A solution containing 0.76 gm (0.0136 mole) of potassium hydroxide and 10 ml of methanol was added dropwise to the diester solution. The mixture formed an immediate emulsion. The emulsion was heated to 65-70° C. and soon thereafter a precipitate began to form. After 30 minutes the reaction was complete. The mixture was cooled to room temperature and the solid collected on a Buchner funnel. The filter cake was washed several times with warm toluene and ether; thereupon the cake was dried in a vacuum oven at 60° C. The yield was 2.85 gm (96%).

NMR (D$_2$O, tetramethylsilane, external standard): $\delta$3.8 (s, 3H), 7.8 (s, 4H).

IR (nujol mull): 1720 cm$^{-1}$ (carbonyl ester).

Preparation of 4-Methoxycarbonylbenzoyl Chloride

This procedure is a modification of the one described by B. W. Hotten (Ind. Eng. Chem. 1957, 49, 1691-4).

Into a three-necked 50 ml round bottom flask equipped with a mechanical stirrer and a reflux condenser topped with a drying tube containing indicating Drierite ® were added 1.39 gm (0.0064 mole) of monopotassium monomethyl terephthalate and 20 ml of toluene. Into this slurry was added dropwise 0.95 gm (0.079 mole) of thionyl chloride. The mixture was heated to 60-70° C. and after two hours there resulted a clear light yellow solution. Heating was continued an additional four hours. IR analysis showed the reaction to be complete after this heating period. To the reaction solution was added an equal volume of ether; soon thereafter the potassium chloride by-product precipitated. After removal of the salt from the ethereal product solution, the acid chloride was obtained as a white solid by solvent stripping. Yield of acid chloride was 82%.

NMR (CDCl$_3$, tetramethylsilane, external standard): $\delta$3.8 (s, 3H), 8.3 (s, 4H). IR (nujol mull): 1730 cm$^{-1}$ (carbonyl ester), 1775 cm$^{-1}$ (carbonyl acid chloride).

Preparation of Sodium 4-(4-methoxycarbonyl)benzoyloxybenzenesulfonate (MCBBS)

This procedure is an adaptation of one described by J. P. Sankey and W. R. Sanderston (U.S. Pat. No. 4,704,236).

To a 100 ml three-necked round bottom flask equipped with a mechanical stirrer and a reflux condenser topped with a nitrogen gas inlet adapter were added 50 ml of decane, 5.0 grams (0.025 mole) of 4-carbomethoxybenzoyl chloride and 4.94 grams (0.0252 mole) of dried sodium 4-hydroxybenzenesulfonate. The mixture was heated to reflux for 22 hours and continuously swept with dry nitrogen. NMR analysis after this heating period showed essentially complete reaction to the desired product. The mixture was cooled to 50° C. and an equal volume of acetone was added. The solid was collected on a filter and subsequently washed with 70 ml of 90:10 ethanol/water solution. The solid was then dried in a vacuum oven. The yield was 8.1 gm (90%).

NMR (DSMO-d$_6$, tetramethylsilane, external standard): $\delta$4.0 (s, 3H), 7.2 (d, 2H), 7.8 (d, 2H), 8.3 (s, 4H).

EXAMPLE 2

Preparation of Diethyl Terephthalate

Into a 250 ml three-necked round bottom flask equipped with a mechanical stirrer and reflux condenser topped with a drying tube containing indicating Drierite ® were added 100 ml of toluene and 40.6 grams (0.20) mole of terephthaloyl chloride. To this solution was added dropwise 18.4 grams (0.40 mole) of ethanol. The reaction solution was heated for two hours at 60-65° C. After this heating period IR analysis showed the complete disappearance of the acid chloride stretch at 1775 cm$^{-1}$. The reaction solution was washed three times with 10% sodium bicarbonate solution and subsequently three times with distilled water. The product solution was dried over magnesium sulfate. After removal of the desiccant the toluene was removed by distillation. The residue crystallized on standing and amounted to 38 grams (86% yield) of diethyl terephthalate.

NMR (acetone-$d_6$, TMS external standard): $\delta$1.4 (t, 6H), 4.4 (q, 4H), 8.0 (s, 4H).

Preparation of Potassium Monoethyl Terephthalate

This compound was prepared by the procedure described for potassium monomethyl terephthalate. Typical reagent levels were as follows: 77.0 gm (0.346 mole) of diethyl terephthalate, 19.4 gm of potassium hydroxide, 150 ml of toluene and 100 ml of ethanol.

After workup, potassium terephthalate was used without further purification.

NMR ($D_2O$, TMS external standard): 1.2 (t, 3H), 4.2 (q, 2H), 7.8 (s, 4H).

Preparation of Monoethyl Terephthaloyl Chloride

This compound was prepared by the procedure described for monomethyl terephthaloyl chloride. Typical reagent levels were as follows: 79.4 gm (0.341 mole) of potassium monoethyl terephthalate, 60.9 gm (0.341 mole) of thionyl chloride and 100 ml of toluene.

After workup, monoethyl terephthaloyl chloride was used without further purification.

IR (nujol mull): 1770 cm$^{-1}$ (acid chloride carbonyl), 1720 cm$^{-1}$

Preparation of Sodium 4-(4-Ethoxycarbonyl)benzoyloxybenzenesulfonate (ECBBS)

This compound was prepared by the procedure described for sodium 4-(4-methoxycarbonyl)benzoyloxybenzenesulfonate. Typical reagent levels were as follows: 35.0 gm (0.18 mole) of sodium 4-hydroxybenzenesulfonate, 70.0 gm (0.243 mole, 74%, remainder potassium chloride) of 4-ethyoxycarbonylbenzoyl chloride and 200 ml of decane.

Workup of the reaction mixture was initiated after 77% conversion was indicated by NMR analysis.

NMR (DSMO-$d_6$, TMS external standard): $\delta$1.2 (T, 3H), 4.2 (q, 2H), 7-7.8 (m, 4H), 8.2 (brd s, 4H).

EXAMPLE 3

Preparation of Dipropyl Terephthalate

This compound was prepared by the procedure described for diethyl terephthalate. Typical reagent levels were as follows: terephthaloyl chloride (81.2g, 0.40 mole), 1-propanol (48.1 g, 0.80 mole) and 100 ml of toluene. Yield was 97% and product was used without further purification.

IR (nujol mull): 1720 cm$^{-1}$ (ester carbonyl).

Preparation of Potassium Monopropyl Terephthalate

This compound was prepared by the procedure described for potassium monomethyl terephthalate. Typical reagent levels were as follows: dipropyl terephthalate (97.3 g, 0.39 mole), potassium hydroxide (22.0g, 0.39 mole), 100 ml of toluene and 200 ml of 1-propanol. After workup 92.0 g of product was recovered which represented a 95% yield.

NMR ($D_2O$, TMS, external standard): $\delta$0.8 (t, 3H), 1.4-1.8 (m, 2H), 4.0 (t, 2H), 7.8 (m, 4H).

Preparation of Monopropyl Terephthaloyl Chloride

This compound was prepared by the procedure described for monomethyl terephthaloyl chloride. Typical reagent levels were as follows: potassium monopropyl terephthalate (49.0g, 0.20 mole), thionyl chloride (29.8g, 0.25 mole) and 100 ml of toluene. The product was used without further purification.

IR (neat): 1720 cm$^{-1}$ (ester carbonyl), 1775 cm$^{-1}$ (acid chloride carbonyl).

Preparation of Sodium 4-(4-Propoxycarbonyl)benzoyloxybenzenesulfonate (PCBBS)

This compound was prepared by the procedure described for MCBBS. Typical reagent levels were as follows: sodium 4-hydroxybenzene sulfonate (17.0 g, 0.097 mole), monopropyl terephthaloyl chloride (30.0 g, 75%, remainder potassium chloride, 0.100 mole) and 100 ml of decane. Workup of the reaction mixture was performed after NMR analysis showed a 63% yield.

NMR (DMSO-$d_6$, TMS external standard): $\delta$1.0 (t, 2H), 1.4-2.0 (m, 2H), 4.2 (t, 2H), 7-7.8 (m, 4H), 8.2 (brd s, 4H).

EXAMPLE 4

Preparation of Dibutyl Terephthalate

This compound was prepared by the procedure described for diethyl terephthalate. Typical reagent levels were as follows: terephthaloyl chloride (40.6 g, 0.20 mole), 1-butanol (29.6g, 0.40 mole), and 100 ml of toluene. Product yield was 75% and was used without further purification.

NMR (acetone-$d_6$, TMS external standard): $\delta$0.6-1.6 (m, 1.4H), 3.9 (t, 4H), 7.7 (s, 4H).

IR (nujol mull): 1720 cm$^{-1}$ (ester carbonyl).

Preparation of Potassium Monobutyl Terephthalate

This compound was prepared by the procedure described for potassium monomethyl terephthalate. Typical reagent levels were as follows: dibutyl terephthalate (10.0 g, 0.036 mole), potassium hydroxide (2.1 g, 0.036 mole), 50 ml of toluene and 20 ml of 1-butanol. After workup 9.4 g was recovered which represented a 96% yield.

NMR ($D_2O$, TMS external standard): $\delta$0.6-1.6 (m, 7H), 4.2 (t, 2H), 8.0 (s, 4H).

Preparation of Monobutyl Terephthaloyl Chloride

This compound was prepared by the procedure described for monomethyl terephthaloyl chloride. Typical reagent levels were as follows: potassium monobutyl terephthalate (10.0 g, 0.0384 mole), thionyl chloride (4.57, 0.0384 mole) and 40 ml of toluene. The yield of product was 8.5 g (92%). This material was used without further purification.

NMR (CDCl$_3$, TMS external standard): $\delta$0.8-1.8 (m, 7H), 4.4 (t, 2H), 8.0 (brd s, 4H).

IR (neat): 1720 cm$^{-1}$ (ester carbonyl), 1770 cm$^{-1}$ (acid chloride).

Preparation of Sodium 4-(4-Butoxycarbonyl)benzoyloxybenzenesulfonate (BCBBS)

This compound was prepared by the procedure described for MCBBS. Typical reagent levels were as follows: monobutyl terephthaloyl chloride (4.5 g, 0.0188 mole), sodium 4-hydroxybenzenesulfonate (2.45 g, 0.0125 mole) and 30 ml of decane. After workup and purification, 4 g (80%) of pure product +was obtained.

NMR (DMSO-d$_6$, TMS external standard): δ0.6–2.0 (m, 7H), 4.3 (t, 2H), 7.2–7.6 (m, 4H), 8.2 (brd s, 4H).

EXAMPLE 5

Preparation of Dihexyl Terephthalate

This compound was prepared by the procedure described for diethyl terephthalate. Typical reagent levels were as follows: terephthaloyl chloride (50.0g, 0.25 mole), 1-hexanol (60.0 g, 0.59 mole) and 100 ml of toluene. Product yield was 71 g (85%) and the material was used without further purification.

NMR (acetone-d$_6$, TMS external standard): δ0.6–2.0 (m, 22H), 4.2 (t, 4H), 8.0 (brd s, 4H).

IR (nujol mull): 1715 cm$^{-1}$ (ester carbonyl).

Preparation of Potassium Monohexyl Terephthalate

This compound was prepared by the method described for potassium monomethyl terephthalate. Typical reagent levels were as follows: dihexyl terephthalate (33.5 g, 0.10 mole), potassium hydroxide (5.6 g, 0.10 mole), 100 ml of toluene and 20 ml of 1-hexanol. After workup 20.2g (70%) of product was recovered.

NNR (D$_2$O, TMS external standard): δ0.6–1.4 (m, 11H), 4.0 (t, 2H), 7.8 (brd s, 4H).

IR (nujol mull): 1720 cm$^{-1}$ (ester carbonyl).

Preparation of Monohexyl Terephthaloyl Chloride

This compound was prepared by the method described for monomethyl terephthaloyl chloride. Typical reagent levels were as follows: potassium monohexyl terephthalate (18.6 g, 0.64 mole), thionyl chloride (9.21 g, 0.774 mole) and 100 ml of toluene. The product was used without further purification.

NMR (CDCl$_3$, TMS external standard): δ0.6–2.0 (m, 11H), 4.4 (t, 2H), 8.2 (brd s, 4H).

IR (neat): 1720 cm$^{-1}$ (ester carbonyl), 1775 cm$^{-1}$ (acid chloride carbonyl).

Preparation of Sodium 4-(4-Hexvloxycarbonyl)benzoyloxybenzenesulfonate (HCBBS)

This compound was prepared by the method described for MCBBS. Typical reagent levels were as follows: monohexyl terephthaloyl chloride (15.0 g, 0.44 mole, 78%, remainder potassium chloride), sodium 4-hydroxybenzenesulfonate (6.6 g, 0.034 mole) and 100 ml of decane. Workup of the reaction mixture was performed after NMR analysis showed an 80% yield.

NMR (DMSO-d$_6$, TMS external standard): δ0.6–2.0 (m, 11H), 4.3 (t, 2H), 7-7.8 (m, 4H), 8.2 (brd s, 4H).

EXAMPLE 6

Preparation of Diphenyl Terephthalate

This compound was prepared by the procedure described for diethyl terephthalate. Typical reagent levels were as follows: terephthaloyl chloride (20.3g, 0.10 mole), phenol (18.9 g, 0.20 mole) and 150 ml of toluene. Product yield was 29 g (91%). After workup, diphenyl terephthalate was used without further purification.

NMR (CDCl$_3$, TMS external standard): δ7–7.6 (m, 10H), 8.4 (brd s, 4H).

Preparation of Potassium Monophenyl Terephthalate

This procedure is an adaptation of one described by R. F. Kovar and F. E. Arnold, J. Poly. Sci. 1976, 14, 2807.

Into a three-necked 50 ml round bottom flask equipped with a mechanical stirrer and a reflux condenser topped with a drying tube containing indicating Drierite ® were added 100 ml of diethylene glycol ether and 3.6 g (0.063 mole) of potassium hydroxide pellets. The mixture was heated to solubilize the alkali fully. To this solution was added 10.0 g (0.0314 mole) of diphenyl terephthalate and the solution was heated to reflux. After 15 minutes the reaction solution was cooled to room temperature whereupon glistening platelets of product began to precipitate. The product was collected and washed with methylene chloride. The crude salt was dissolved in water and any remaining insoluble material was removed by filtration. Pure product was obtained by freeze-drying the aqueous product solution. Isolated yield was 6.8 g (80%).

NMR (D$_2$O, TMS external standard): δ7–8.2 (m).

Preparation of Monophenyl Terephthaloyl Chloride

This compound was prepared in a manner similar to that for monomethyl terephthaloyl chloride. However, in this procedure the thionyl chloride was used as both reagent and solvent. Typical reagent levels were as follows: potassium monophenyl terephthalate (6.8 g, 0.024 mole) and 7 ml of thionyl chloride. After workup the product was used without further purification.

NMR (CDCl$_3$, TMS external standard): δ7.4–8.3 (m)

IR (neat) 1734 cm$^{-1}$ (ester carbonyl) 1778 cm$^{-1}$ (acid chloride carbonyl).

Preparation of Phenyl 4-Cholyoxycarbonylbenzoate, Chloride Salt (PCCB)

Into a three-necked 50 ml round bottom flask equipped with a mechanical stirrer and a reflux condenser topped with a drying tube containing indicating Drierite ® were added to 50 ml of acetonitrile, monophenyl terephthaloyl chloride, 3.5 g (0.010 mole, 78%, remainder potassium chloride, 0.010 mole) and 1.6 g (0.0115 mole) of choline chloride. The mixture was maintained at reflux for three hours. NMR analysis indicated essentially quantitative conversion to product. The solid was collected by filtration and recrystallized from isopropanol/water (90:10). An isolated yield of 3.5 g (83%) was obtained.

NMR (D$_2$O, TMS external standard): δ3.2 (s, 9H), 3.4–3.8 (m, 2H), 4.4–4.8 (m, 2H), 7.76 (m, 5H), 8.2 (brd s, 4H).

EXAMPLE 7

Preparation of Monocholyl Glutaric Acid, Chloride Salt

Into a three-necked 50 ml round bottom flask equipped with a mechanical stirrer and a reflux condenser topped with a drying tube containing indicating Drierite ® were added 2.0g (0.018 mole) of glutaric anhydride, 2.45 g (0.018 mole) of dry choline chloride and 50 ml of acetonitrile. The resultant mixture was heated at reflux for 12 hours. During the heating period the mixture became a homogeneous solution. Isolation of the product was achieved by cooling the reaction solution to ice water temperatures and collecting the product crystal precipitate by filtration. Aside from washing the solid with ether, no further purification was performed. A 4.1 g (92%) yield was realized.

NMR (D$_2$O, TMS external standard): δ1.6–2.6 (m, 6H), 3.1 (s, 9H), 3-5–3.8 (m, 2H), 4.3–4.7 (m, 2H).

Preparation of Monocholyl Mono-4-sulfophenyl Glutarate (MCMSG)

Into a three-necked 50 ml round bottom glass equipped with a mechanical stirrer and a reflux condenser topped with a drying tube containing indicating Drierite® added 3.3 g (0.013 mole) of monocholyl glutaric acid and 16.3 g (0.14 mole) of thionyl chloride. The mixture was heated to reflux and after several minutes a solution was obtained. The reaction progress was monitored by infrared analysis, i.e., observing the decrease in the —OH stretch absorption intensity and the increase in the acid chloride carbonyl stretch at 1785 cm$^{-1}$. The reaction was determined to be complete after 45 minutes at reflux. Solvent and excess thionyl chloride were removed by distillation. To the residual viscous liquid, essentially product acid chloride, were then added 20 ml of acetonitrile and 2.5 g (0.013 mole) of sodium 4-hydroxybenzenesulfonate. The mixture was brought to reflux and after 16 hours NMR analysis indicated that quantitative conversion to product had been achieved. The solid was collected by filtration while the reaction mixture was still warm and then washed twice with acetone. Pure product was obtained by recrystallization from ethanol/water. Isolated yield was 4.1 g (85%).

NMR (D$_2$O, TMS external standard): $\delta$2.0–3.0 (m, 6H), 3.2 (s, 9H), 3.6–3.8 (m, 2H), 4.4–4.8 d(m, 2H), 7.2–8.1 (m, 4H).

EXAMPLE 8

Preparation of Monocholyl Succinic Acid, Chloride Salt

This compound was prepared by the procedure described for monocholyl glutaric acid, chloride salt. Typical reagent levels were as follows: succinic anhydride (2.0 g, 0.020 mole), choline chloride (2.8 g, 0.020 mole), and 50 ml of acetonitrile. The yield of isolated product was 4.6 g (96%). No further purification was performed.

NMR (D$_2$O, TMS external standard): $\delta$2.4 (brd s, 4H), 3.1 (s, 9H), 3.5–3.8 (m, 2H) 4.2–4.6 (m, 2H).

Preparation of Monocholyl Mono-4-sulfophenyl Succinate (MCMSS)

This compound was prepared by the procedure described for MCMSG. Typical reagent levels were as follows: monocholyl succinic acid, chloride salt (3.3 g, 0.0–14 mole) 10 ml of thionyl chloride, sodium 4-hydroxybenzenesulfonate (2.6 g, 0.014 mole) and 20 ml of acetonitrile.

NMR (D$_2$O, TMS external standard): $\delta$1.6–2.6 (m, 4H), 3.1 (s, H), 3.5–3.8 (m, 2H), 4.3–4.7 (m, 2H), 7.0–8.0 (m, 4H).

EXAMPLE 9

Preparation of Monocholyl Phthalate, Chloride Salt

This compound was prepared by the procedure described for monocholyl glutaric acid, chloride salt. Typical reagent levels were as follows: phthalic anhydride (14.0 g, 0.10 mole), choline chloride (14.8 g, 0.–10 mole) and 65 ml of acetonitrile. The yield of isolated product was 2-10 g (73%). No further purification of the product was performed aside from several acetonitrile washes.

NMR (DMSO-d$_6$, TMS external standard): $\delta$3.05 (s, 9H), 3.6–3.9 (m, 2H), 4.5–4.8 (m, 2H), 7.6 (brd s, 4H).

Preparation of 4-(2-Cholyoxycarbonyl)benzoyloxybenzenesulfonate (2-CCBBS)

This compound was prepared by the procedure described for MCMSG. Typical reagent levels were as follows: monocholyl phthalate, chloride salt (8.0 g, 0.028 mole), thionyl chloride (4.8 g, 0.040 mole), sodium 4-hydroxybenzenesulfonate (4.95 g, 0.025 mole) and 40 ml of acetonitrile.

NMR (D$_2$O/CD$_3$CN, TMS external standard): $\delta$3.05 (s, 9H), 3.6–3.8 (m, 2H), 4.5–4.8 (m, 2H), 7.2–8.1 (m, 9H).

EXAMPLE 10

Peracid Generation From Precursors

Peroxyacid precursors described herein can be used to generate peroxyacid bleaches in basic aqueous solution containing a source of hydrogen peroxide and, optimally, may contain typical detergent ingredients. Peroxyacid generation was demonstrated by adding a premeasured sample of precursor to 500 ml aqueous buffer solution at the desired pH, heated to 40° C. in a thermo-jacketed beaker, and containing the approximate level of hydrogen peroxide (added as either 3% hydrogen peroxide or sodium perborate monohydrate). The hydrogen peroxide source was added just prior to addition of the precursor. Twenty-five milliliter aliquots of solution were withdrawn from the beaker at regular intervals and were added to a 250 ml titration flask containing crushed ice (100 g), glacial acetic acid (25 ml) and 5% aqueous potassium iodide (10 ml). The iodine produced was titrated immediately with 0.005N sodium thiosulfate solution. Time zero was taken as the point of introduction of precursor into the peroxide solution. Precursor perhydrolysis experiments were generally carried out for a maximum of 15 minutes.

Since hydrogen peroxide itself contributes to the total oxygen in these titrations, controls or "blanks" were obtained by carrying out a perhydrolysis experiment in the absence of precursor. These hydrogen peroxide blanks were subtracted from the total active oxygen titration in the presence of bleach precursor to give the level of active oxygen produced by precursor perhydrolysis.

Percarboxylic acid generation was determined at pH 10. Carbonate buffer was used for these experiments. Adjustment of the buffer system at 40° C. to the exact pH was carried out with I M hydrochloric acid.

Table I lists the peracid acid yields as a percent theoretical from the peracid precursors prepared in the previous examples.

TABLE I

| Precursor | [H$_2$O$_2$]/[Precursor] | 1 Minute | 8 Minutes | 15 Minutes |
|---|---|---|---|---|
| 1. MCBBS | 1:1 | 76% | 91% | 93% |
|  | 8:1 | 86% | 94% | 87% |
| 2. ECBBS | 1:1 | 62% | 66% | 66% |
|  | 8:1 | 73% | 68% | 59% |
| 3. PCBBS | 1:1 | 56% | 60% | 58% |
|  | 8:1 | 51% | 48% | 43% |
| 4. BCBBS | 1:1 | 62% | 66% | 65% |
|  | 8:1 | 59% | 58% | 53% |
| 5. HCBBS | 1:1 | 58% | 70% | 57% |
|  | 8:1 | 64% | 60% | 52% |
| 6. 4-CCBBS | 1:1 | 64% | 66% | 64% |

TABLE I-continued

| Precursor | [H$_2$O$_2$]/[Precursor] | 1 Minute | 8 Minutes | 15 Minutes |
|---|---|---|---|---|
| | 8:1 | 63% | 68% | 64% |
| 7. 2-CCBBS | 1:1 | 64% | 74% | 70% |
| | 8:1 | 97% | 59% | 36% |
| 8. MCMSS | 1:1 | 78% | 82% | 76% |
| | 8:1 | 88% | 89% | 86% |
| 9. MCMSG | 1:1 | 74% | 75% | 75% |
| | 8:1 | 82% | 85% | 82% |

Conditions: 40° C., pH 10.0, [Precursor] = 6.2 × 10$^{-4}$ M, [H$_2$O$_2$] = 6.2 × 10$^{-4}$ M, or 5.0 × 10$^{-3}$ M.

EXAMPLE 11

Bleaching From Peroxyacid Precursor/Peroxide Systems

The stain bleaching ability of peroxyacids, generated from the synthesized precursors was demonstrated on common stains such as tea and spaghetti sauce. Typically, cotton test pieces (4 in.×4 in.) stained with the appropriate stain were washed in a Terg-O-Tometer in 1 L of aqueous solution containing a given level of bleach precursor, hydrogen peroxide, buffer, and surfactant (generally sodium dodecylbenzenesulfonate).

Washes were carried out at 40° C. for 15 minutes. Stain bleaching was measured reflectometrically using a Colorgard System/05 Reflectometer. Bleaching is indicated by an increase in reflectance, reported as ΔR. In general, a ΔR of one unit is perceivable in a paired comparison while ΔR of two units is perceivable monadically. In reporting the reflectance change, the change in reflectance caused by general detergency and bleaching by the excess hydrogen peroxide has been accounted for. Thus ΔR can actually be expressed as: ΔR=(Reflectance of stained fabric washed with precursor/H$_2$O$_2$ and detergent - reflectance of stained fabric before washing) - (reflectance of stained fabric washed with H2O2 and detergent alone - reflectance of stained fabric before washing).

In the case of spaghetti stain, bleaching is measured as "Δb" where the quantity "Δb" is the change in the b-axis of the Hunter color scale. The spaghetti stain is initially yellow and loses color with bleaching and thus bleaching produces a negative change in b. Since peroxide-only controls were also carried out with the spaghetti sauce stains, percarboxylic acid bleaching is actually reported as "Δb".

It can be seen that bleaching from all the cationic peroxycarboxylic acid bleaches is excellent, with one exception, giving substantial tea stain removal between pH 9 and 10. Only minor bleach activity is seen with 2-CCBBS. The non-cationic disubstituted terephthalate peracid precursors similarly provided strong tea stain bleaching at typical wash pHs. Further it can be seen that by increasing the hydrophobicity of the ester moiety of the peroxyacid, good oily stain bleaching can be affected. Compare the spaghetti sauce bleaching by HCBBS and BCBBS versus MCBBS and ECBBS.

TABLE II

| Precursor | [H$_2$O$_2$] M | pH | Bleach Performance ΔR Tea | Spaghetti |
|---|---|---|---|---|
| MCBBS | 1.86 × 10$^{-3}$ | 9 | 8.8 | 0.6 |
| | 1.86 × 10$^{-3}$ | 10 | 5.4 | — |
| | 6.25 × 10$^{-3}$ | 9 | 8.5 | 0.8 |
| | 6.25 × 10$^{-3}$ | 10 | 5.9 | — |
| ECBBS | 1.86 × 10$^{-3}$ | 9 | 9.8 | 1.0 |
| | 1.86 × 10$^{-3}$ | 10 | 5.6 | 0 |
| | 6.25 × 10$^{-3}$ | 9 | 10.0 | 0.7 |
| | 6.25 × 10$^{-3}$ | 10 | 7.0 | 0.6 |
| PCBBS | 1.86 × 10$^{-3}$ | 9 | 8.2 | 2.4 |
| | 1.86 × 10$^{-3}$ | 10 | 5.5 | 0.9 |
| | 6.25 × 10$^{-3}$ | 9 | 9.4 | 1.2 |
| | 6.25 × 10$^{-3}$ | 10 | 6.7 | 0.9 |
| BCBBS | 1.86 × 10$^{-3}$ | 9 | 9.0 | 9.0 |
| | 1.86 × 10$^{-3}$ | 10 | 6.7 | 1.4 |
| | 6.25 × 10$^{-3}$ | 9 | 10.7 | 5.4 |
| | 6.25 × 10$^{-3}$ | 10 | 7.5 | 1.4 |
| HCBBS | 1.86 × 10$^{-3}$ | 9 | 8.8 | 12.8 |
| | 1.86 × 10$^{-3}$ | 10 | 7.0 | 7.8 |
| | 6.25 × 10$^{-3}$ | 9 | 10.0 | 10.4 |
| | 6.25 × 10$^{-3}$ | 10 | 10.5 | 6.0 |
| PCCB | 1.86 × 10$^{-3}$ | 9 | 12.5 | — |
| | 1.86 × 10$^{-3}$ | 10 | 11.8 | — |
| | 6.25 × 10$^{-3}$ | 9 | 15.8 | — |
| | 6.25 × 10$^{-3}$ | 10 | 12.0 | — |
| 2-CCBBS | 1.86 × 10$^{-3}$ | 9 | 2.0 | — |
| | 1.86 × 10$^{-3}$ | 10 | 2.0 | — |
| | 6.25 × 10$^{-3}$ | 9 | 2.7 | — |
| | 6.25 × 10$^{-3}$ | 10 | 2.0 | — |
| MCMSS | 1.86 × 10$^{-3}$ | 9 | 19.5 | — |
| | 1.86 × 10$^{-3}$ | 10 | 13.0 | — |
| | 6.25 × 10$^{-3}$ | 9 | 20.3 | — |
| | 6.25 × 10$^{-3}$ | 10 | 14.5 | — |
| MCMSG | 1.86 × 10$^{-3}$ | 9 | 18.5 | — |
| | 1.86 × 10$^{-3}$ | 10 | 15.7 | — |
| | 6.25 × 10$^{-3}$ | 9 | 20.0 | — |
| | 6.25 × 10$^{-3}$ | 10 | 16.0 | — |

[Precursor] = 6.2 × 10$^{-4}$ M, wash temperature 40° C.

The foregoing description and Examples illustrate selected embodiments of the present invention. In light thereof, various modifications will be suggested to one skilled in the art all of which are within the spirit and purview of this invention.

What is claimed is:

1. A bleach precursor compound having the formula:

$$X-OC-A-C-Z$$
(with two C=O groups)

wherein:

A is a C$_1$–C$_{12}$ radical which is selected from the group consisting of alkylene, alkenylene, alkynylene, cycloalkylene, cycloalkenylene, alkarylene, arylene and mixtures thereof;

X is selected from the group consisting of a quaternized heterocyclic ring system and a quaternary ammonium substituted C$_1$–C$_{20}$ radical the hydrocarbyl portion of which is different from that of Z and selected from the group consisting of alkyl, alkenyl, alkynyl, cycloalkyl, cycloalkenyl, alkaryl, and aryl; and Z is a leaving group whose conjugate acid has a pKa from about 6 to 13.

2. The precursor of claim 1 wherein Z is a leaving group whose conjugate acid has a pKa from about 7 to 11.

3. The precursor of claim 2 wherein the pKa ranges from about 8 to 11..

4. The precursor of claim 1 wherein X is a group whose pKa is greater than 14.

5. The precursor of claim 4 wherein the pKa ranges from about 15 to 30.

6. The precursor of claim 2 wherein Z is selected from the group consisting of:

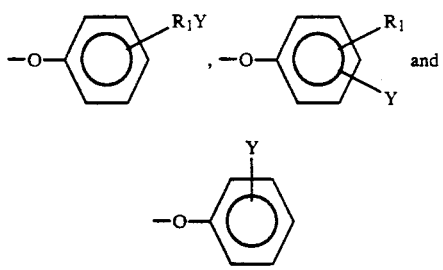

wherein $R_1$ is a $C_1$–$C_{12}$ alkyl or alkylene group or hydrogen; Y is a water solubilizing group selected from the group consisting of $-SO_3^-M^+$, $-COO^{-1}M^+$, $-N^+(R)_3B^-$ and mixtures thereof; wherein $M^+$ is an alkali metal, ammonium or alkyl or hydroxyalkyl substituted ammonium cation; and $B^-$ is a halide, phosphate, sulfate, methyl sulfate or acetate anion.

7. The precursor of claim 2 wherein Z has the formula:

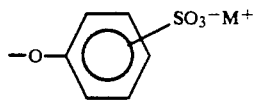

8. The precursor of claim 1 wherein the heterocyclic ring system is selected from the group consisting of pyridine, morpholine, pyrrolidine, piperidine and piperazine.

9. The precursor of claim 1 wherein X is a cholyl group.

10. The precursor of claim 1 which is formed from diacids selected from the group consisting of phthalic, terephthalic, succinic, glutaric, azelaic, isophthalic, and dodecanedioic acids.

11. The precursor of claim 1 wherein the compound is phenyl 4-cholyloxycarbonylbenzoate, chloride salt.

12. The precursor of claim 1 wherein the compound is 4-(2-cholyloxycarbonyl)benzoyloxybenzenesulfonate.

13. The precursor of claim 1 wherein the compound is monocholyl mono-4-sulfophenyl succinate.

14. The precursor of claim 1 wherein the compound is monocholyl mono-4-sulfophenyl glutarate.

15. A bleach composition comprising:
  (i) from 1 to 60% of a peroxygen compound capable of yielding hydrogen peroxide in an aqueous solution;
  (ii) from 0.1 to 40% of a bleach precursor having the formula I according to claim 1;
  (iii) from 0 to 50% of a surfactant; and
  (iv) from 0 to 80% of a detergent builder.

16. The composition of claim 15 wherein the surfactant ranges from 4 to 50% and the detergent builder ranges from 5 to 70% by weight.

17. The composition of claim 15 wherein Z is a leaving group whose conjugate acid has a pKa from 6 to 13.

18. The precursor of claim 17 wherein the pKa ranges from about 8 to 11.

19. The precursor of claim 15 wherein X is a group whose pKa is greater than 14.

20. The precursor of claim 15 wherein the pKa ranges from about 15 to 30.

21. The precursor of claim 15 wherein Z is selected from the group consisting of:

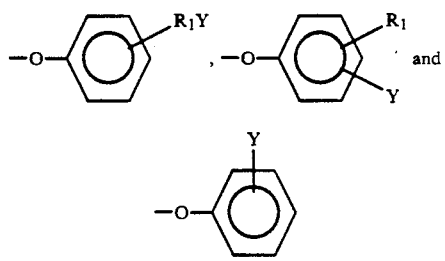

wherein $R_1$ is a $C_1$–$C_{12}$ alkyl or alkylene group or hydrogen; Y is a water solubilizing group selected from the group consisting of $-SO_3^-M^+$, $-COO-M^+$, $-N^{+(R)}{}_3B^-$ and mixtures thereof; wherein $M^+$ is an alkali metal, ammonium or alkyl or hydroxyalkyl substituted ammonium cation; and $B^-$ is a halide, phosphate, sulfate, methyl sulfate or acetate anion.

22. The precursor of claim 15 wherein Z has the formula:

23. The precursor of claim 20 wherein the heterocyclic ring system is selected from the group consisting of pyridine, morpholine, pyrrolidine, piperidine and piperazine.

24. The composition of claim 15 wherein X is a cholyl group.

25. The composition of claim 15 which is formed from diacids selected from the group consisting of phthalic, terephthalic, succinic, glutaric, azelaic, isophthalic, and dodecanedioic acids.

26. The composition of claim 15 wherein the compound is phenyl 4-cholyloxycarbonylbenzoate, chloride salt.

27. The composition of claim 15 whrein the compound is 4-(2-cholyloxycarbonyl)benzoyloxybenzenesulfonate.

28. The composition of claim 15 wherein the compound is monocholyl mono-4-sulfophenyl succinate.

29. The composition of claim 15 wherein the compound is monocholyl mono-4-sulfophenyl glutarate.

* * * * *